United States Patent [19]
Tanner et al.

[11] Patent Number: 6,024,942
[45] Date of Patent: *Feb. 15, 2000

[54] PHOTOPROTECTIVE COMPOSITIONS

[75] Inventors: Paul Robert Tanner, Maineville; Julie Ann Wagner; Christopher Irwin, both of Cincinnati, all of Ohio

[73] Assignee: The Procter & Gamble Company, Cincinnati, Ohio

[ * ] Notice: This patent is subject to a terminal disclaimer.

[21] Appl. No.: 08/986,956

[22] Filed: Dec. 8, 1997

Related U.S. Application Data

[63] Continuation-in-part of application No. 08/599,202, Feb. 9, 1996, Pat. No. 5,759,202.

[51] Int. Cl.[7] .................................................... A61K 7/42
[52] U.S. Cl. ................................................ 424/59; 424/63
[58] Field of Search .............................. 424/78.03, 59, 424/63

[56] References Cited

U.S. PATENT DOCUMENTS

| | | | |
|---|---|---|---|
| 2,798,053 | 7/1957 | Brown | 260/2.2 |
| 3,937,810 | 2/1976 | Mathur et al. | 424/62 |
| 4,096,240 | 6/1978 | Mathur | 424/59 |
| 4,411,886 | 10/1983 | Hostettler | 424/70 |
| 4,509,949 | 4/1985 | Huang | 586/558 |
| 4,699,924 | 10/1987 | Durrant et al. | 514/588 |
| 4,732,930 | 3/1988 | Tanaka et al. | 524/742 |
| 4,822,604 | 4/1989 | Knoll et al. | 424/70 |
| 4,877,805 | 10/1989 | Kligman | 514/381 |
| 4,888,342 | 12/1989 | Kligman | 514/419 |
| 4,948,577 | 8/1990 | Hara | 424/59 |
| 4,960,764 | 10/1990 | Figueroa, Jr. et al. | 514/174 |
| 5,091,171 | 2/1992 | Yu et al. | 424/642 |
| 5,100,660 | 3/1992 | Hawe et al. | 424/78.35 |
| 5,296,500 | 3/1994 | Hillebrand | 514/562 |
| 5,385,938 | 1/1995 | Yu et al. | 514/557 |
| 5,389,677 | 2/1995 | Yu et al. | 514/557 |
| 5,411,741 | 5/1995 | Zaias | 424/450 |
| 5,411,991 | 5/1995 | Shander et al. | 514/665 |
| 5,476,651 | 12/1995 | Meybeck et al. | 424/59 |
| 5,514,374 | 5/1996 | Bonte et al. | 424/195.1 |
| 5,520,919 | 5/1996 | Lerner | 424/401 |
| 5,556,887 | 9/1996 | Lerner | 514/772.6 |
| 5,591,437 | 1/1997 | Bonte et al. | 424/195.1 |
| 5,759,524 | 6/1998 | Tanner | 424/78.02 |

FOREIGN PATENT DOCUMENTS

| | | | |
|---|---|---|---|
| 2100405 | 1/1994 | Canada | A61K 7/42 |
| 0 193 387 A2 | 9/1986 | European Pat. Off. | A61K 7/42 |
| A2 202621 | 11/1986 | European Pat. Off. | A61K 7/06 |
| 0 330 369 A1 | 8/1989 | European Pat. Off. | A61K 7/48 |
| A2 347145 | 12/1989 | European Pat. Off. | A61K 9/26 |
| 0 396422A1 | 11/1990 | European Pat. Off. | A61K 7/48 |
| 0 512814A1 | 11/1992 | European Pat. Off. | A61K 7/48 |
| 0 579 079 | 1/1994 | European Pat. Off. | A61K 7/42 |
| 2096712 | 2/1972 | France | A16K 27/00 |
| 2608424 | 6/1988 | France | A61K 7/42 |
| 2136697 | 2/1973 | Germany | A61L 23/00 |
| 2242553 | 3/1974 | Germany | A61K 7/00 |
| 4018964 | 7/1991 | Germany | A61K 31/505 |
| 4327679A1 | 2/1995 | Germany | A61K 7/48 |
| 144276 | 4/1978 | India | A61L 23/00 |
| 61-037712 | 2/1986 | Japan | A61K 7/00 |
| 4-26610 | 1/1992 | Japan | A61K 7/00 |
| 5-078383 | 3/1993 | Japan | C07H 15/26 |
| 6-065044 | 3/1994 | Japan | A61K 7/48 |
| 6-107531 | 4/1994 | Japan | A61K 7/48 |
| 7-277939 | 10/1995 | Japan | A61K 7/48 |
| 9-012471 | 1/1997 | Japan | A61K 38/00 |
| 1370236 | 10/1974 | United Kingdom | A61K 7/00 |
| 1533119 | 11/1978 | United Kingdom | A61K 7/00 |
| 2230186A | 10/1990 | United Kingdom | A61K 7/44 |
| 89/10738 A1 | 11/1989 | WIPO | A61K 7/42 |
| 92/13566 | 8/1992 | WIPO | A61K 47/32 |
| 92/19214 | 11/1992 | WIPO | A61K 7/00 |
| 93/07903 A1 | 4/1993 | WIPO | A61K 47/32 |
| 94/02176 | 2/1994 | WIPO | A61K 47/32 |
| WO 94/09756 | 5/1994 | WIPO | A61K 7/48 |
| 94/15580 A1 | 7/1994 | WIPO | A61K 7/42 |
| 95/03781 | 2/1995 | WIPO | A61K 7/48 |
| 95/22311 A1 | 8/1995 | WIPO | A61K 7/48 |
| WO 96/37420 | 11/1996 | WIPO | B65D 81/32 |

OTHER PUBLICATIONS

Caplus, JP 56044046 B4, Oct. 16, 1981, abstract only.
Caplus, JP 09067227 A2, Mar. 11, 1997, abstract only.
G.M. Eccleston, "Multi–phase Oil–in–Water Emulsions," *J. Soc. Cosmet. Chem.* 41, pp. 1–22 (Jan./Feb. 1990).
W.P. Smith, "Hydroxy Acids and Skin Aging," Walter Smith Consultants, Soap/Cosmetics/Chemical Specialties for Sep. 1993.
G.H. Dahms, "New Oil–in–Water Concepts Based on Emulsifiers Derived from Renewable Raw Materials," ICI Surfactants, RP 58/91E.
Dr. P. Loll, "Liquid Crystals in Cosmetics Emulsions," ICI Surfactants, RP 94–93E.
G.H. Dahms, "Properties of O/W Emulsions with Anisotropic Lamellar Phases," *Cosmetics & Toiletries,* vol. 101, Nov. 1986.

*Primary Examiner*—Peter F. Kulkosky
*Attorney, Agent, or Firm*—George W. Allen; Loretta J. Henderson; Fumiko Tsuneki

[57] ABSTRACT

The present invention relates to leave on, skin care compositions, comprising: (a) from about 0.1% to about 30% of a sunscreen active, (b) from about 0.5% to about 20% of a hydrophobic, structuring agent, (c) from about 0.2% to about 10% of a hydrophilic surfactant, (d) from about 0.1% to about 5% of a thickening agent, (e) from about 0.1% to about 25% of a skin lightening agent and (f) water. These compositions are useful for providing (i) protection to human skin from the harmful effects of ultraviolet radiation and (ii) a skin lightening benefit.

21 Claims, No Drawings

PHOTOPROTECTIVE COMPOSITIONS

CROSS-REFERENCE INFORMATION

This is a continuation-in-part of patent application Ser. No. 08/599,202 filed on Feb. 9, 1996, now U.S. Pat. No. 5,759,202.

TECHNICAL FIELD

The present invention relates to compositions which are useful for providing protection to the skin of humans from the harmful effects of ultraviolet radiation in combination with a skin lightening or skin evening benefit. In particular it relates to stable, cosmetic, aqueous-containing compositions having gel networks, liquid crystalline phases, or both. These compositions also contain a thickening agent. Without being limited by theory, it is believed that the aqueous phase of these compositions contain relatively-low levels of free water. In other words, the water is believed to be bound as part of the gel network or liquid crystals. These compositions are found to be especially useful for delivering sunscreen actives to the skin.

BACKGROUND OF THE INVENTION

The damaging effects of sunlight on skin are well documented. Contrary to what most people believe, it is not necessary that one sunbathe to suffer the ill-effects of excessive UV exposure. In fact, significant damage can be done just by routine day to day activities in sunlight. The major short term hazard of prolonged exposure to sunlight is erythema, i.e. sunburn. In addition to the short term hazard are long term hazards such as malignant changes in the skin surface. Numerous epideminologic studies demonstrate a strong relationship between sunlight exposure and human skin cancer. Another long term hazard of ultraviolet radiation is premature aging of the skin. This condition is characterized by wrinkling and pigment changes of the skin, along with other physical changes such as cracking, telangiectasis, solar dermatoses, ecchymoses, and loss of elasticity. The adverse effects associated with exposure to UV radiation are more fully discussed in DeSimone, "Sunscreen and Suntan Products," *Handbook of Nonprescription Drugs*, 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation," *International Journal of Cosmetic Science*, 4, pp. 15–24 (1982); and U.S. Pat. No. 4,387,089, DePolo, issued Jun. 7, 1983; all of these references being incorporated by reference herein in their entirety. Hence, although the immediate effects of ultraviolet radiation may be cosmetically and socially gratifying, the long term hazards are cumulative and potentially serious.

The fact that these effects are taken seriously by the general public is suggested by considering the sun protection product market. This market has grown considerably in recent years and many new products are introduced each year. What used to be looked upon as a seasonal business is no longer seen as such. Sunscreen agents are now included in a diversity of personal care products, particularly cosmetic type products which are worn on a daily basis.

Many consumers also desire a skin lightening benefit in combination with photoprotective benefits. Skin lightening results in a more even skin appearance by an overall lightening of basal skin tone and hyperpigmented lesions. Thus, a composition providing a combination of photoprotective benefits and skin lightening benefits is highly desirable.

Sunscreen formulas are generally based on oil-in-water and water-in-oil emulsion systems. However, many conventional systems suffer from disadvantages such as inefficient UV protection, chemical and physical instability, and unattractive aesthetic properties when applied to the skin. It has surprisingly been found that the photoprotective compositions of the present invention overcome these disadvantages. These compositions comprise a sunscreen active, a stable, hydrophobic, structuring agent, a hydrophilic surfactant, a thickening agent, and water. Without being limited by theory, it is believed that these compositions contain gel network structures, liquid crystal structures, or both. It is believed that these gel networks and liquid crystals tend to bind the available water in the composition, thereby rendering the water less available for contributing to the instability and decomposition of the active ingredients. It is also found that these compositions are well-suited for formulating with highly polar materials, e.g., inorganic sunscreen agents such as titanium dioxide, zinc oxide, and iron oxide, which are often used to enhance or boost the UV protection effects of organic type sunscreen agents. Additionally, it is found that these compositions have good aesthetic, i.e. skin feel properties. Finally, it is found that these compositions can also be easily formulated with skin lightening agents.

Therefore, it is an object of the present invention to provide novel compositions for providing protection from the harmful effects of UV radiation to the skin.

It is a further object of the present invention to provide photoprotective compositions comprising water, and having gel networks, liquid crystals or both.

It is a further object of the present invention to provide photoprotective compositions which are both chemically and physically stable.

It is a further objective of the present invention to provide photoprotective compositions which have an aesthetically appealing feel when applied to the skin.

It is a further objective of the present invention to provide photoprotective compositions which also provide a skin lightening benefit.

These and other objects will become readily apparent from the detailed description which follows.

SUMMARY OF THE INVENTION

The present invention relates to photoprotective compositions that are useful for protecting human skin from the harmful effects of UV radiation comprising:

(a) from about 0.1% to about 30% of a sunscreen active;

(b) from about 0.5% to about 20% of a hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 40° C.;

(c) from about 0.2% to about 10% of a hydrophilic surfactant selected from the group consisting of nonionic surfactants, anionic surfactants, cationic surfactants, zwitterionic surfactants, amphoteric surfactants, and mixtures thereof;

(d) from about 0.1% to about 5% of a thickening agent selected from the group consisting of carboxylic acid polymers, crosslinked polyacrylate polymers, polyacrylamide polymers, polysaccharides, gums, crosslinked vineyl ether/maleic anhydride copolymers, crosslinked poly(N-vinylpyrrolidones), and mixtures thereof, and (e) from about 0.1% to about 25% of a skin lightening agent; and (f) from about 25% to about 99.1% water.

In further embodiments, the present invention also relates to methods for providing protection to human skin from the harmful effects of UV radiation, and methods for providing a skin lightening or a skin evening benefit.

All percentages and ratios used herein are by weight of the total composition. All measurements made are at 25° C., unless otherwise designated. All weight percentages, unless otherwise indicated, are on an actives weight basis. The invention hereof can comprise, consist of, or consist essentially of, the essential as well as optional ingredients and components described herein.

DETAILED DESCRIPTION OF THE INVENTION

The compositions of the present invention are useful for providing protection to human skin from the harmful effects of ultraviolet radiation. These compositions are in the form of oil-in-water emulsions whereby the oil phase and the water phase can contain, in addition to the essential components described herein, a variety of ingredients known in the art. These compositions are in the form of topical, leave-on compositions. The compositions herein are useful for topical application to the skin.

The term "topical application," as used herein, means to apply or spread the compositions to the surface of the skin.

The term "pharmaceutically acceptable," as used herein, means that the compositions or components thereof so described are suitable for use in contact with human skin without undue toxicity, incompatibility, instability, allergic response, and the like.

The compositions of the present invention have complex rheological characteristics. These compositions have physical properties characteristic of oil-in-water emulsions, liquid crystals, and crystalline gel networks. Without being limited by theory, it is believed that these compositions have low levels of free water, such that most of the water is bound up with liquid crystals or gel networks. It is found that these compositions are useful as vehicles for compositions which are labile in aqueous solution or dispersion. It is also found that these compositions are useful for formulating with actives which are highly polar, such as physical sunscreen agents such as titanium dioxide, zinc oxide, iron oxide, and the like.

The nature of liquid crystals, the formation of liquid crystals, the properties and advantages of liquid crystals, and gel networks are described further in G. Dahms, "Properties of O/W Emulsions with Anisotropic Lamellar Phases," 101 *Cosmetics & Toiletries* 113–115, (1986); P. Loll, "Liquid Crystals in Cosmetic Emulsions," *ICI Surfactants' Publication RP94-93E*; and G. M. Eccleston, "Multiple-Phase Oil-In-Water Emulsion," 41 *J. Soc. Cosmet. Chem.* 1–22, (January/February 1990); all of which are incorporated herein by reference in their entirety.

The compositions herein have desirable aesthetic and elegant properties, such as a rich and creamy, yet non-greasy, skin feel. These compositions can span a broad range of consistencies from thin lotions to heavy creams. These compositions typically have viscosities ranging from about 100 cps to about 500,000 cps, preferably from about 3,000 cps to about 200,000 cps, more preferably from about 5000 cps to about 150,000 cps, as measured at a temperature of 25° C. with a Brookfield Synchro-Lectric Viscometer Model D. The compositions can span a wide range of pH values.

Even though buffers can be utilized to help maintain the pH of the emulsion compositions, these are not required components, but are merely optional ingredients.

The compositions of the present invention comprise the following essential components. These components should be pharmaceutically acceptable.

Sunscreen Agent

The compositions of the present invention comprise from about 0.1% to about 30%, more preferably from about 0.5% to about 25%, and most preferably from about 1% to about 20% of the compositions of the present invention. Mixtures of sunscreen agents can also be used. Exact amounts of sunscreen agent will vary depending upon the sunscreen or sunscreens chosen and the desired Sun Protection Factor (SPF) to be achieved. SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. See *Federal Register*, Vol. 43, No. 166, pp. 38206–38269, Aug. 25, 1978, which is incorporated herein by reference in its entirety.

A wide variety of sunscreen agents are useful herein. These sunscreen agents include both organic compounds and their salts as well as inorganic particulate materials. Without being limited by theory, it is believed that sunscreen agents provide protection from ultraviolet radiation by one or more of the following mechanisms including absorption, scattering, and reflection of the ultraviolet radiation. Non-limiting examples of these sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; U.S. Pat. No. 5,160,731, to Sabatelli et al., issued Nov. 3, 1992; U.S. Pat. No. 5,138,089, to Sabatelli, issued Aug. 11, 1992; U.S. Pat. No. 5,041,282, to Sabatelli, issued Aug. 20, 1991; U.S. Pat. No. 4,999,186, to Sabatelli et al., issued Mar. 12, 1991; U.S. Pat. No. 4,937,370, to Sabatelli, issued Jun. 26, 1990; and Segarin, et al., at Chapter VIII, pages 189 et seq., of *Cosmetics Science and Technology*; all of these documents being incorporated herein by reference in their entirety. Preferred among the sunscreen agents are those selected from the group consisting of 2-ethylhexyl p-methoxycinnamate, octyl salicylate, octocrylene, oxybenzone, 2-ethylhexyl N,N-dimethylaminobenzoate, p-aminobenzoic acid, 2-phenyl-benzimidazole-5-sulfonic acid, homomenthyl salicylate, DEA p-methoxycinnamate, 4,4'methoxy-t-butyldibenzoylmethane, 4-isopropyldibenzoylmethane, 3-(4-methylbenzylidene) camphor, 3-benzylidene camphor, 4-N,N-dimethylaminobenzoic acid ester with 2,4-dihydroxybenzophenone, 4-N,N-dimethylaminobenzoic acid ester with 2-hydroxy-4-(2-hydroxyethoxy) benzophenone, 4-N,N-dimethylaminobenzoic acid ester with 4-hydroxydibenzoyl- methane, 4-N,N-direthylaminobenzoic acid ester with 4-(2-hydroxyethoxy) dibenzoylmethane, 4-N,N-di(2-ethylhexyl)- aminobenzoic acid ester with 2,4-dihydroxybenzophenone, 4-N,N-di(2-ethylhexyl)aminobenzoic acid ester with 2-hydroxy-4-(2-hydroxyethoxy)benzophenone, 4-N,N-di(2-ethylhexyl) aminobenzoic acid ester with 4-hy-droxydibenzoylmethane, 4-N,N-di(2-ethylhexyl)aminobenzoic acid ester with 4-(2-hydroxyethoxy)dibenzoylmethane, 4-N,N-(2-ethylhexyl) methylaminobenzoic acid ester with 2,4-dihydroxybenzophenone, 4-N,N-(2-ethylhexyl) methylaminobenzoic acid ester with 2-hydroxy-4-(2-hydroxyethoxy)benzophenone, 4-N,N-(2-ethylhexyl)

methylaminobenzoic acid ester with 4-hydroxydibenzoylmethane, 4-N,N-(2-ethylhexyl) methylaminobenzoic acid ester with 4-(2-hydroxyethoxy) dibenzoylmethane, titanium dioxide, zinc oxide, iron oxide, and mixtures thereof.

More preferred for use in the compositions described herein are the sunscreen agents selected from the group consisting of 2-ethylhexyl N,N-dimethyl-p-aminobenzoate, 2-ethylhexyl p-methoxycinnamate, octocrylene, octyl salicylate, homomenthyl salicylate, p-aminobenzoic acid, oxybenzone, 2-phenylbenzimidazole-5-sulfonic acid, DEA p-methoxycinnamate, 4,4'-methoxy-t-butyldibenzoylmethane, 4-isopropyl dibenzoylmethane, 3-(4-methylbenzylidene) camphor, 3-benzylidene camphor, 4-N,N-(2-ethylhexyl)methylaminobenzoic acid ester with 4-(2-hydroxyethoxy)dibenzoylmethane, titanium dioxide, zinc oxide, iron oxide, and mixtures thereof Even more preferred for use in the compositions described herein are the sunscreen agents selected from the group consisting of 2-ethylhexyl N,N-dimethyl-p-aminobenzoate, 2-ethylhexyl p-methoxycinnamate, octocrylene, octyl salicylate, oxybenzone, 2-phenylbenzimidazole-5-sulfonic acid, 4,4'-methoxy-t-buyldibenzoylmethane, 3-(4-methylbenzylidene) camphor, 3-benzylidene camphor, 4-N,N-(2-ethylhexyl) methylaminobenzoic acid ester with 4-(2-hydroxyethoxy) dibenzoylmethane, titanium dixoide, zinc oxide, iron oxide, and mixtures thereof.

Most preferred for use in the compositions of the present invention are the sunscreen agents selected from he group consisting of 2-ethylhexyl p-methoxycinnamate, 4,4'-methoxy-t-buyldibenzoylmethane, zinc oxide, and mixtures thereof.

Structuring Agent

The present invention comprises from about 0.5% to about 20%, preferably from about 1% to about 10%, and more preferably from about 1% to about 5%, of a hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 40° C. Without being limited by theory, it is believed that these structuring agents are useful to assist in the formation of the rheological characteristic of the composition which contribute to the hydrolytic stability of the composition of the present invention. In particular structuring agents assist in the formation of the liquid crystalline gel network structures.

The preferred structuring agents of the present invention are selected from the group consisting of stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearyl alcohol, cetyl alcohol, behenyl alcohol, steareth-2, and mixtures thereof.

Hydrophilic Surfactant

The compositions of the present invention comprise from about 0.2% to about 10%, preferably from about 0.2% to about 6%, and more preferably from about 0.2% to about 3% of at least one hydrophilic surfactant. Without being limited by theory, it is believed that the hydrophilic surfactant disperses the hydrophobic materials, i.e. the structuring agent, in the water phase. The surfactant, at a minimum, must be hydrophilic enough to disperse in water.

The surfactants useful herein can include any of a wide variety of cationic, anionic, zwitterionic, and amphoteric surfactants disclosed in prior patents and other references. See McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

The exact surfactant chosen will depend upon the pH of the composition and the other components present.

Preferred for use herein are nonionic surfactants. Among the nonionic surfactants that are useful herein are those that can be broadly defined as condensation products of long chain alcohols, e.g. C8–30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100. Other nonionic surfactants are the condensation products of alkylene oxides with 2 moles of fatty acids (i.e. alkylene oxide diesters of fatty acids). These materials have the general formula $RCO(X)_nOOCR$ wherein R is a C10–30 alkyl group, X is —OCH$_2$CH$_2$—(i.e. derived from ethylene glycol or oxide) or —OCH$_2$CHCH$_3$—(i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula $R(X)_nOR'$ wherein R is a C10–30 alkyl group, X is —OCH$_2$CH$_2$—(i.e. derived from ethylene glycol or oxide) or —OCH$_2$CHCH$_3$—(i.e. derived from propylene glycol or oxide), and n is an integer from about 6 to about 100 and R' is H or a C10–30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are C10–30 alkyl groups, X is —OCH$_2$CH$_2$ (i.e. derived from ethylene glycol or oxide) or —OCH$_2$CHCH$_3$— (derived from propylene glycol or oxide), and n is an integer from about 6 to about 100. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof Still other useful nonionic surfactants include polyhydroxy fatty acid amide surfactants corresponding to the structural formula:

wherein: R$^1$ is H, C$_1$–C$_4$ alkyl, 2-hydroxyethyl, 2-hydroxypropyl, preferably C$_1$–C$_4$ aklyl, more preferably methyl or ethyl, most preferably methyl; R$^2$ is C$_5$–C$_{31}$ alkyl or alkenyl, preferably C$_7$–C$_{19}$ alkyl or alkenyl, more preferably C$_9$–C$_{17}$ alkyl or alkenyl, most preferably C$_{11}$–C$_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the R$^2$CO— moiety is derived from coconut oil fatty acids). Processes for making compositions containing polyhydroxy fatty acid amides are disclosed, for example, in G. B. Pat. Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Preferred among the nonionic surfactants are those selected from the group consisting of steareth-21, ceteareth-20, ceteareth-12, sucrose cocoate, steareth-100, PEG-100 stearate, and mixtures thereof.

A wide variety of cationic surfactants useful herein are disclosed in U.S. Pat. No. 5,151,209, to McCall et al., issued Sep. 29, 1992; U.S. Pat. No. 5,151,210, to Steuri et al., issued Sep. 29, 1992; U.S. Pat. No. 5,120,532, to Wells et al., issued Jun. 9, 1992; U.S. Pat. No. 4,387,090, to Bolich, issued Jun. 7, 1983; U.S. Pat. No. 3,155,591, Hiflfer, issued Nov. 3, 1964; U.S. Pat. No. 3,929,678, to Laughlin et al., issued Dec. 30, 1975; U.S. Pat. No. 3,959,461, to Bailey et al., issued May 25, 1976; McCutcheon's, *Detergents & Emulsifiers*, (North American edition 1979) M.C. Publishing Co.; and Schwartz, et al., *Surface Active Agents, Their Chemistry and Technology*, New York: Interscience Publishers, 1949; all of these documents being incorporated herein by reference in their entirety. The cationic surfactants useful herein include cationic ammonium salts such as those having the formula:

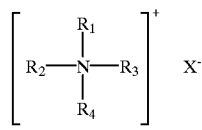

wherein R$_1$, is an alkyl group having from about 12 to about 30 carbon atoms, or an aromatic, aryl or alkaryl groups having from about 12 to about 30 carbon atoms; R$_2$, R$_3$, and R$_4$ are independently selected from hydrogen, an alkyl group having from about 1 to about 22 carbon atoms, or aromatic, aryl or alkaryl groups having from about 12 to about 22 carbon atoms; and X is any compatible anion, preferably selected from the group consisting of chloride, bromide, iodide, acetate, phosphate, nitrate, sulfate, methyl sulfate, ethyl sulfate, tosylate, lactate, citrate, glycolate, and mixtures thereof. Additionally, the alkyl groups of R$_1$, R$_2$, R$_3$, and R$_4$ can also contain ester and/or ether linkages, or hydroxy or amino group substituents (e.g., the alkyl groups can contain polyethylene glycol and polypropylene glycol moieties).

More preferably, R$_1$ is an alkyl group having from about 12 to about 22 carbon atoms; R$_2$ is selected from H or an alkyl group having from about 1 to about 22 carbon atoms; R$_3$ and R$_4$ are independently selected from H or an alkyl group having from about 1 to about 3 carbon atoms; and X is as described previously.

Most preferably, R$_1$ is an alkyl group having from about 12 to about 22 carbon atoms; R$_2$, R$_3$, and R$_4$ are selected from H or an alkyl group having from about 1 to about 3 carbon atoms; and X is as described previously.

Alternatively, other useful cationic emulsifiers include amino-amides, wherein in the above structure R$_1$ is alternatively R$_5$CONH—(CH$_2$)$_n$—, wherein R$_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamaidopropyl PG-dimonium chloride phosphate, behenamidopropyl PG dimonium chloride, stearmnidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl dimethyl ammonium chloride, dimethyl ammonium chloride, dimethyl ammonium bromide, dilauryl ammonium chloride, dilauryl ammonium bromide, distearyl ammonium chloride, distearyl ammonium bromide, dimethyl methyl ammonium chloride, dimethyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include dimethyl ammonium chloride, dimethyl ammonium methyl sulfate, di(hydrogenated tallow) dimethyl ammonium chloride, di(hydrogenated tallow) dimethyl ammonium acetate, dimethyl dipropyl ammonium phosphate, dimethyl ammonium nitrate, di(coconutalkyl)dimethyl ammonium chloride, di(coconutalayl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearmnidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from the group consisting of behenamidopropyl PG dimonium chloride, dilauryl dimethyl ammonium chloride, distearyl dimethyl ammonium chloride, dimethyl ammonium chloride, dipalmityl dimethyl ammonium chloride, distearyl dimethyl ammonium chloride, stearamidopropyl PG-dimonium chloride phosphate, stearmnidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Most preferred cationic surfactants are those selected from the group consisting of behenamidopropyl PG dimonium chloride, dilauryl dimethyl ammonium chloride, distearyl dimethyl ammonium chloride, dimethyl ammonium chloride, dipalmityl dimethyl ammonium chloride, and mixtures thereof.

A wide variety of anionic surfactants are also useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula RCO—OCH$_2$CH$_2$SO$_3$M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae ROSO$_3$M and RO(C$_2$H$_4$O)$_x$SO$_3$M, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R_1—SO_3—M$$

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas RN[CH$_2$)$_m$CO$_2$M]$_2$ and RNH(CH$_2$)$_m$CO$_2$M wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Also useful herein as amphoteric or zwitterionic surfactants are the betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the RCONH(CH$_2$)$_3$ radical is attached to the nitrogen atom of the betaine), oleyl betaine (available as amphoteric Velvetex OLB-50 from Henkel), and coamidopropyl betaine (available as Velvetex BK-35 and BA-35 from Henkel).

Other useful amphoteric and zwitterionic surfactants include the sultaines and hydroxysultaines such as coamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Thickening Agent

The compositions of the present invention can also comprise from about 0.1% to about 5%, more preferably from about 0.1% to about 3%, and most preferably from about 0.25% to about 2% of a thickening agent.

Nonlimiting classes of thickening agents include those selected from the group consisting of carboxylic acid polymers, crosslinked polyacrylate polymers, polyacrylamide polymers, polysaccharides, gums, vinyl ether/maleic anhydride copolymers, crosslinked poly(N-vinylpyrrolidones), and mixtures thereof. Preferred thickening agents are those selected from the group consisting of carboxylic acid polymers, crosslinked polyacrylate polymers, polyacrylamide polymers, and mixtures thereof. More preferred thickening agents are those selected form the group consisting of crosslinked polyacrylate polymers, polyacrylamide polymers, and mixtures thereof. See, U.S. Pat. No. , 4,387,107, to Klein et al., issued Jun. 7, 1983 and "Encyclopedia of Polymer and Thickeners for Cosmetics," R. Y. Lochhead and W. R. Fron, eds., *Cosmetics & Toiletries*, vol. 108, pp. 95–135 (May 1993), which list a variety of thickening or gelling agents, and which are all incorporated herein by reference in their entirety.

Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred carboxylic acid polymers are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ alkyl, —CN, —COOH, and mixtures thereof). The second type of polymer is a crosslinked copolymer having a first monomer selected from the group consisting of an acrylic acid monomer or derivative thereof (as just described in the previous sentence), a short chain alcohol (i.e., a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof, and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers, the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters, $C_{1-4}$ alcohol ethacrylate esters, and mixtures thereof, with the $C_{1-4}$ alcohol acrylate esters, $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are both incorporated by reference herein in their entirety. See also, *CTFA International Cosmetic Ingredient Dictionary*, fourth edition, 1991, pp. 12 and 80; which are also incorporated herein by reference in their entirety.

Examples of commercially available homopolymers of the first type useful herein include the carbomers, which are homopolymers of acrylic acid crosslinked with allyl ethers of sucrose or pentaerytritol. The carbomers are available as the Carbopol® 900 series from B. F. Goodrich. Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Pemulen TR-1, and Pemulen TR-2, from B.F. Goodrich. In other words, examples of carboxylic acid polymer thickeners useful herein are those selected from the group consisting of carbomers, acrylates/$C_{10}$–$C_{30}$ alkyl acrylate crosspolymers, and mixtures thereof.

Crosslinked Polyacrylate Polymers

The crosslinked polyacrylate polymers useful as thickeners or gelling agents include both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

The crosslinked polyacrylate polymers are high molecular weight materials that can be characterized by the general formula: $(A)_1(B)_m(C)_n$ and comprise the monomer units $(A)_1$, $(B)_m$, and $(C)_n$, wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer that is polymerizable with (A) or (B), for example a monomer having a carbon-carbon double bond or other such polymerizable functional group, l is an integer of 0 or greater, m is an integer of 0 or greater, n is an integer of 0 or greater, but where either l or m, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1$–$C_8$, preferably $C_1$–$C_5$, more preferably $C_1$–$C_3$, and most preferably $C_1$–$C_2$. When quaternzied, the polymers are preferably quaternized with short chain alkyls, i.e., $C_1$–$C_8$, preferably $C_1$–$C_5$, more preferably $C_1$–$C_3$, and most preferably $C_1$–$C_2$. The acid addition salts refer to polymers having protonated amino groups. Acid addition salts can be performed through the use of halogen (e.g. chloride), acetic, phosphoric, nitric, citric, or other acids.

These $(A)_l(B)_m(C)_n$ polymers also comprise a crosslinking agent, which is most typically a material containing two or more unsaturated functional groups. The crosslinking agent is reacted with the monomer units of the polymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g. viscosifying effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about 500 ppm of the total weight of the polymer on a weight/weight basis.

The intrinsic viscosity of the crosslinked polymer, measured in one molar sodium chloride solution at 25° C., is generally above 6, preferably from about 8 to about 14. The molecular weight (weight average) of the crosslinked polymers hereof is high, and is believed to typically be between about 1 million and about 30 million. The specific molecular weight is not critical and lower or higher weight average molecular weights can be used as long as the polymer retains its intended viscosifying effects. Preferably, a 1.0% solution of the polymer (on an actives basis) in deionized water will have a viscosity at 25° C. of at least about 20,000 cP, preferably at least about 30,000 cP, when measured at 20 RPM by a Brookfield RVT (Brookfield Engineering Laboratories, Inc. Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified. When the polymer contains (C) monomer, the molar proportion of (C) monomer, based on the total molar amount of (A), (B), and (C), can be from 0% to about 99%. The molar proportions of (A) and (B) can each be from 0% to 100%. When acrylamide, is used as the (C) monomer, it will preferably be used at a level of from about 20% to about 99%, more preferably from about 50% to about 90%.

Where monomer (A) and (B) are both present, the ratio of monomer (A) to monomer (B) in the final polymer, on a molar basis, is preferably from about 99:5 to about 15:85, more preferably from about 80:20 to about 20:80. Alternatively, in another class of polymers, the ratio is from about 5:95 to about 50:50, preferably from about 5:95 to about 25:75.

In another alternative class of polymers, the ratio (A):(B) is from about 50:50 to about 85:15. Preferably the ratio (A):(B) is about 60:40 to about 85:15, most preferably about 75:25 to about 85:15.

Most preferred is where monomer (A) is not present and the ratio of monomer (B):monomer (C) is from about 30:70 to about 70:30, preferably from about 40:60 to about 60:40 and most preferably from about 45:55 to about 55:45.

Cationic polymers that are useful herein that are especially preferred are those conforming to the general structure $(A)_l(B)_m(C)_n$ wherein l is zero, (B) is methyl quaternized dimethylaminoethyl methacrylate, the ratio of (B):(C) is from about 45:55 to about 55:45, and the crosslinking agent is methylenebisacrylamide. An example of such a cationic polymer is one that is commercially available as a mineral oil dispersion (which can also include various dispersing aids such as PPG-1 trideceth-6) under the trademark Salcare® SC92 from Allied Colloids Ltd. (Norfolk, Va.). This polymer has the proposed CTFA designation, "Polyquaternium 32 (and) Mineral Oil".

Other cationic polymers useful herein, are those not containing acrylamide or other (C) monomers, that is, n is zero. In these polymers the (A) and (B) monomer components are as described above. An especially preferred group of these non-acrylamide containing polymers is one in which l is also zero. In this instance the polymer is essentially a homopolymer of a dialkylaminoalkyl methacrylate monomer or its quaternary ammonium or acid addition salt. These diaklylaminoalkyl methacrylate polymers preferably contain a crosslinking agent as described above.

A cationic polymer, which is essentially a homopolymer, useful herein is one conforming to the general structure $(A)_l(B)_m(C)_n$ wherein l is zero, (B) is methyl quaternized dimethylaminoethyl methacrylate, n is zero, and the crosslinking agent is methylenebisacrylamide. An example of such a homopolymer is commercially available as a mixture containing approximately 50% of the polymer, approximately 44% mineral oil, and approximately 6% PPG-1 trideceth-6 as a dispersing aid, from Allied Colloids Ltd, (Norfolk, Va.) under the trademark Salcare® SC95. This polymer has recently been given the CTFA designation "Polyquaternium 37 (and) Mineral Oil (and) PPG-1 Trideceth-6".

Polyacrylamide Polymers

Also useful herein are polyacrylamide polymers, especially non-ionic polyacrylamide polymers including substituted branched or unbranched polymers. These polymers can be formed from a variety of monomers including acrylamide and methacrylamide which are unsubstituted or subtituted with one or two alkyl groups (preferably $C_1$ to $C_5$). Preferred are acrylate amide and methacrylate amide monomers in which the amide nitrogen is unsubstituted, or substituted with one or two $C_1$ to $C_5$ alkyl groups (preferably methyl, ethyl, or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. These polymers have a molecular weight greater than about 1,000,000 preferably greater than about 1,5000,000 and range up to about 30,000,000. Most preferred among these polyacrylamide polymers is the non-ionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

Polysaccharides

A wide variety of polysaccharides are useful herein. By "polysaccharides" are meant gelling agents containing a backbone of repeating sugar (i.e. carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroyxalkylated (preferably hydroxyethylated or hydroxypropylated) to form a hydroxyalkylated cellulose which is then further modified with a C10–C30 straight chain or branched chain alkyl group through an ether linkage. Typically these polymers are ethers of C10–C30 straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof.

Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1→3) linked glucose units with a (1→6) linked glucose every three units, a commercially available example of which is Clearogel™ CS11 from Michel Mercier Products Inc. (Mountainside, N.J.).

Gums

Other additional thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Crosslinked Vinyl Ether/Maleic Anhydride Copolymers

Other additional thickening and gelling agents useful herein include crosslinked copolymers of alkyl vinyl ethers and maleic anhdride. In these copolymers the vinyl ethers are represented by the formula $R-O-CH=CH_2$ wherein R is a C1–C6 alkyl group, preferably R is methyl. Preferred crosslinking agents are C4–C20 dienes, preferably C6 to C16 dienes, and most preferably C8 to C12 dienes. A particularly preferred copolymer is one formed from methyl vinyl ether and maleic anhydride wherein the copolymer has been crosslinked with decadiene, and wherein the polymer when diluted as a 0.5% aqueous solution at pH 7 at 25° C. has a viscosity of 50,000–70,000 cps when measured using a Brookfield RTV viscometer, spindle #7 at 10 rpm. This copolymer has the CTFA designation PVM/MA decadiene crosspolymer and is commercially available as Stabileze™ 06 from International Specialty Products (Wayne N.J.).

Crosslinked Poly(N-vinylpyrrolidones)

Crosslinked polyvinyl(N-pyrrolidones) useful herein as additional thickening and gelling agents and include those described in U.S. Pat. No. 5,139,770, to Shih et al, issued Aug. 18, 1992, and U.S. Pat. No. 5,073,614, to Shih et al., issued Dec. 17, 1991, both patents of which are incorporated by reference herein in their entirety.

These gelling agents typically contain from about 0.25% to about 1% by weight of a crosslinking agent selected from the group consisting of divinyl ethers and diallyl ethers of terminal diols containing from about 2 to about 12 carbon atoms, divinyl ethers and diallyl ethers of polyethylene glycols containing from about 2 to about 600 units, dienes having from about 6 to about 20 carbon atoms, divinyl benzene, vinyl and allyl ethers of pentaerythritol, and the like. Typically, these gelling agents have a viscosity from about 25,000 cps to about 40,000 cps when measured as a 5% aqueous solution at 25° C. using a Brookfield RVT viscometer with Spindle #6 at 10 rpm. Commercially available examples of these polymers include ACP-1120, ACP-1179, and ACP-1180, available from International Specialty Products (Wayne, N.J.).

Skin Lightening Agents

The compositions of the present invention can preferably comprise from about 0.001% to about 40%, preferably from about 0.001% to about 30%, and more preferably from about 0.001% to about 25%, most preferably from about 1% to about 15% of a skin lightening agent. It is believed that these skin lightening agents even skin appearance by an overall lightening of basal skin tone and hyperpigmented lesions. If a salt of one of the skin lightening agents is used, the levels of the thickening agent can be increased within ranges disclosed herein to maintain acceptable viscosity.

The *CTFA Cosmetic Ingredient Handbook*, Fifth Edition, 1993, which is incorporated by reference herein in its entirety, describes a wide variety of skin lightening agents useful herein. Examples of skin lightening agents useful herein include, but are not limited to, Vitamin $B_3$ compounds and derivatives thereof; kojic acid and derivatives thereof; L-ascorbic acid and derivatives thereof; extract of placenta; arbutin and derivatives thereof; and mixtures thereof. The following skin lightening agents can by used individually or in combination to provide the maximum skin lightening benefit.

Vitamin $B_3$ Compounds

The compositions of the present invention can comprise a safe and effective amount of a vitamin $B_3$ compound. The vitamin $B_3$ compound enhances the skin appearance benefits of the present invention. As used herein, "vitamin $B_3$ compound" means a compound having the formula:

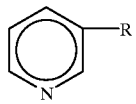

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including nicotinyl amino acids, nicotinyl alcohol esters of carboxylic acids, nicotinic acid N-oxide and niacinamide N-oxide.

Suitable esters of nicotinic acid include nicotinic acid esters of $C_1$–$C_{22}$, preferably $C_1$–$C_{16}$, more preferably $C_1$–$C_6$ alcohols. The alcohols are suitably straight-chain or branched chain, cyclic or acyclic, saturated or unsaturated (including aromatic), and substituted or unsubstituted. Nonlimiting examples of esters of nicotinic acid include tocopherol nicotinate and inositol hexanicotinate; tocopherol nicotinate is preferred.

Other derivatives of the vitamin $B_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1–C18). Specific examples of such derivatives include nicotinuric acid ($C_8H_8N_2O_3$) and nicotinyl hydroxamic acid ($C_6H_6N_2O_2$), which have the following chemical structures:

nicotinuric acid:

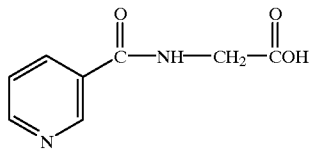

nicotinyl hydroxamic acid:

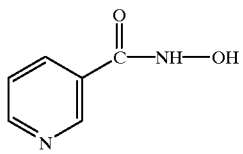

Exemplary nicotinyl alcohol esters include nicotinyl alcohol esters of the carboxylic acids salicylic acid, acetic acid, glycolic acid, palmitic acid and the like. Other non-limiting examples of vitamin $B_3$ compounds useful herein are 2-chloronicotinamide, 6-aminonicotinamide, 6-methylnicotinamide, n-methyl-nicotinamide, n,n-dethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Examples of the above vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin $B_3$ compounds may be used herein. Preferred vitamin $B_3$ compounds are niacinamide and tocopherol nicotinate. Niacinamide is more preferred.

Salts of the vitamin $B_3$ compound are also useful herein. Nonlimiting examples of salts of the vitamin $B_3$ compound useful herein include organic or inorganic salts, such as inorganic salts with anionic inorganic species (e.g., chloride, bromide, iodide, carbonate, preferably chloride), and organic carboxylic acid salts (including mono-, di- and tri-C1–C18 carboxylic acid salts, e.g., acetate, salicylate, glycolate, lactate, malate, citrate, preferably monocarboxylic acid salts such as acetate). These and other salts of the vitamin $B_3$ compound can be readily prepared by the skilled artisan, for example, as described by W. Wenner, "The Reaction of L-Ascorbic and D-Iosascorbic Acid with Nicotinic Acid and Its Amide", J. Organic Chemistry, Vol. 14, 22–26 (1949), which is incorporated herein by reference. Wenner describes the synthesis of the ascorbic acid salt of niacinamide.

In a preferred embodiment, the ring nitrogen of the vitamin $B_3$ compound is substantially chemically free (e.g., unbound and/or unhindered), or after delivery to the skin becomes substantially chemically free ("chemically free" is hereinafter alternatively referred to as "uncomplexed"). More preferably, the vitamin $B_3$ compound is essentially uncomplexed. Therefore, if the composition contains the vitamin $B_3$ compound in a salt or otherwise complexed form, such complex is preferably substantially reversible, more preferably essentially reversible, upon delivery of the composition to the skin. For example, such complex should be substantially reversible at a pH of from about 5.0 to about 6.0. Such reversibility can be readily determined by one having ordinary skill in the art.

More preferably the vitamin $B_3$ compound is substantially uncomplexed in the composition prior to delivery to the skin. Exemplary approaches to minimizing or preventing the formation of undesirable complexes include omission of materials which form substantially irreversible or other complexes with the vitamin $B_3$ compound, pH adjustment, ionic strength adjustment, the use of surfactants, and formulating wherein the vitamin $B_3$ compound and materials which complex therewith are in different phases. Such approaches are well within the level of ordinary skill in the art.

Thus, in a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. The vitamin $B_3$ compound in the compositions hereof having a pH of from about 4 to about 9, preferably from about 4 to about 8.5, typically contain less than about 50% of the salt form.

The vitamin $B_3$ compound may be included as the substantially pure material, or as an extract obtained by suitable physical and/or chemical isolation from natural (e.g., plant) sources. The vitamin $B_3$ compound is preferably substantially pure, more preferably essentially pure.

L-ascorbic Acid and its Derivatives

The compositions of the present invention can comprise a safe and effective amount of ascorbic acid or a derivative thereof. Preferably, the ascorbic acid is L-ascorbic acid. Nonlimiting examples of useful derivatives of ascrobic acid include magnesium ascorbyl phosphate and ascorbyl glucosamine.

Kojic Acid and its Derivatives

The compositions of the present invention can comprise a safe and effective amount of kojic acid or a derivative thereof.

Hydroquinone and its Derivatives

The compositions of the present invention can comprise a safe and effective amount of hydroquinone or a derivative thereof.

Extract of Placenta

The compositions of the present invention can comprise a safe and effective amount of extract of placenta.

Arbutin and its Derivatives

The compositions of the present invention can comprise a safe and effective amount of arbutin or a derivative thereof. Nonlimiting examples of a useful derivative of arbutin are 4-[(tetrahydro-2H-pyran-2-yl)oxy]phenol, 4-[(1-ethoxyethyl)oxy]phenol, 4-[(tetrahydro-2H-thiopyran-2-yl)oxy]phenol, 2-fluoro-4-[(tetrahydro-2H-pyran-2-yl)oxy]phenol, and 4-[(tetrahydrofuran-2-yl)oxy].

Water

The compositions of the present invention comprise from about 25% to about 99.1%, more preferably from about 50% to about 95%, and most preferably from about 60% to about 90% water. The exact amount of water in the formulation will vary with the ranges of the required and optional components chosen.

Optional Components

The compositions of the present invention can comprise a wide range of additional components. These additional components should be pharmaceutically acceptable. The *CTFA Cosmetic Ingredient Handbook*, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, absorbents, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin-conditioning agents (humectants, miscellaneous, and occlusive).

Some nonlimiting examples of these additional components cited in the *CTFA Cosmetic Ingredient Handbook*, as well as other materials useful herein, include the following: vitamins and derivatives thereof (e.g. tocopherol, tocopherol acetate, retinoic acid, retinol, retinoids, and the like); polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; other anti-acne medicaments (e.g., resorcinol, sulfur, salicylic acid, erythromycin, zinc, and the like); antioxidants; chelators and sequestrants; skin treating agents such as alpha-hydroxy acids such as lactic acid and glycolic acid, and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabolol, dipotassium glycyrrhizinate and the like; and skin conditioning agents such as the propoxylated glycerols described in U.S. Pat. No. 4,976,953, to Orr et al., issued Dec. 11, 1990, which is incorporated by reference herein in its entirety.

Methods For Protecting The Skin From UV Radiation

The compositions of the present invention are useful for providing protection to human skin from the harmful effects of UV radiation. To protect the skin a safe and effective amount of the composition is applied to the skin. By "safe and effective amount" is meant an amount effective for providing the benefits of the present invention, i.e. protection from the harmful effects of UV radiation, without any undue toxicity, allergic, or other unwanted side effects. By "protection" is meant that these compositions attenuate or reduce the amount of UV radiation reaching the skin's surface. Quantities of composition which are typically applied to provide protection are about but not limited to, about 2 $mg/cm^2$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

| Photoprotective Compositions | | | |
|---|---|---|---|
| Ingredient | I WT. % | II WT. % | III WT. % |
| Octyl methoxycinnamate | 6.0 | 6.0 | 6.0 |
| Zinc Oxide | 5.0 | 5.0 | 5.0 |
| Isohexadecane | 4.0 | 4.0 | 4.0 |
| Glycerin | 3.0 | 6.0 | 6.0 |
| Polyquaternium 37 (and ) mineral oil (and) PPG-1-trideceth-6[1] | 2.0 | 0.0 | 0.0 |
| Polyacrylamide (and) C13–14 isoparaffin (and) laureth-7[2] | 0.0 | 2.25 | 2.0 |
| Dimethicone (and) dimethiconol[3] | 0.0 | 1.0 | 1.0 |
| Cetyl palmitate | 0.0 | 1.0 | 0.0 |
| Isopropyl palmitate | 0.0 | 1.0 | 2.0 |
| Cyclomethicone (and) dimethiconol[4] | 0.5 | 0.0 | 0.0 |
| Steareth-21 | 0.9 | 0.45 | 0.9 |
| Stearyl alcohol | 0.8 | 1.5 | 1.5 |
| Cetyl alcohol | 0.8 | 1.5 | 1.5 |
| Cyclomethicone (and) dimethicone copolyol[5] | 0.5 | 0.0 | 0.0 |
| Benzyl alcohol | 0.5 | 0.5 | 0.5 |
| Methyl paraben | 0.25 | 0.25 | 0.25 |
| Vitamin E acetate | 0.2 | 0.5 | 0.5 |

-continued

Photoprotective Compositions

| Ingredient | I WT. % | II WT. % | III WT. % |
|---|---|---|---|
| Propyl paraben | 0.15 | 0.15 | 0.15 |
| Disodium EDTA | 0.13 | 0.13 | 0.13 |
| DEA Oleth-3 phosphate | 0.1 | 0.1 | 0.1 |
| Niacinamide | 0.0 | 0.0 | 3.0 |
| Steareth-2 | 0.1 | 0.05 | 0.1 |
| Water | QS 100 | QS 100 | QS 100 |

[1]Available as Salcare SC95 from Allied Colloids.
[2]Available as Sepigel 305 from Seppic, Inc.
[3]Available as Dow Corning Q2-1403 fluid from Dow Corning Corporation.
[4]Available as Dow Corning Q2-1401 fluid from Dow Corning Corporation.
[5]Available as Dow Corning Q2-3225C from Dow Corning Corporation.

The above compositions are prepared as follows:

The emulsion water phase is prepared by combining the glycerin, methylparaben, disodium EDTA, and water in a mixing vessel. Next, a zinc dispersion premix is prepared by combining the isohexadecane, octyl methoxycinnamate, and DEA oleth-3 phosphate in a separate vessel, and warming slightly to solubilize the DEA oleth-3 phosphate. The zinc oxide is then stirred into the mix of oils for about several minutes, and this zinc dispersion is then milled. Next, the remaining oil phase ingredients (cetyl palmitate, isopropyl palmitate, steareth-21, stearyl alcohol, cetyl alcohol, Dow Corning Q2-3225C, vitamin E acetate, propylparaben, and steareth-2) are mixed into the zinc dispersion.

Both the water phase and oil phase are then heated to 70–80° C., and the oil phase is slowly added to the water phase while the system is milled to form an emulsion. The emulsion is then cooled with stirring. When the system reaches about 60° C., the Salcare SC95, Sepigel 305, Dow Corning Q2-1401, and Dow Corning Q2-1403 are added, and the product is milled again to disperse the polymers and silicones (when present). The system is then further cooled with stirring. The benzyl alcohol is then added when the product reaches about 48° C., and the product is poured into appropriate containers at about 30° C.

These compositions are useful for applying to human skin to provide protection from the harmfull effects of UV radiation.

What is claimed is:

1. A photoprotective composition comprising:
   (a) from about 0.1% to about 30% of a sunscreen active;
   (b) from about 0.5% to about 20% of a hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 40° C.;
   (c) from about 0.2% to about 10% of a hydrophilic surfactant selected from the group consisting of nonionic surfactants, anionic surfactants, cationic surfactants, zwitterionic surfactants, amphoteric surfactants, and mixtures thereof;
   (d) from about 0.1% to about 5% of a thickening agent selected from the group consisting of carboxylic acid polymers, crosslinked polyacrylate polymers, polyacrylamide polymers, polysaccharides, gums, crosslinked vinyl ether/maleic anhydride copolymers, crosslinked poly(N-vinylpyrrolidones), and mixtures thereof;
   (e) from about 0.001% to about 25% of a skin lightening agent; and
   (f) from about 25% to about 99.1% water.

2. A composition according to claim 1 wherein said skin lightening agent is selected from the group consisting of Vitamin $B_3$ compounds and derivatives thereof; L-ascorbic acid and derivatives thereof, kojic acid and derivatives thereof; extract of placenta; arbutin and derivatives thereof; and mixtures thereof.

3. A composition according to claim 2 wherein said skin lightening agent is a Vitamin $B_3$ compound selected from the group consisting of niacinamide, tocopheral nicotinate, and mixtures thereof.

4. A composition according to claim 1 wherein said sunscreen active is selected from the group consisting of 2-ethylhexyl N,N-dimethyl-p-aminobenzoate, 2-ethylhexyl p-methoxycinnamate, octocrylene, octyl salicylate, homomenthyl salicylate, p-aminobenzoic acid, oxybenzone, 2-phenylbenzimidazole-5-sulfonic acid, DEA p-methoxycinnamate, 4,4'-methoxy-t-butyidibenzoylmethane, 4-isopropyl dibenzoylmethane, 3-(4-methylbenzylidene)camphor, 3-benzylidene camphor, titanium dioxide, zinc oxide, iron oxide, and mixtures thereof.

5. A composition according to claim 4 wherein said thickening agent is selected from the group consisting of carboxylic acid polymers, crosslinked polyacrylate polymers, polyacrylamide polymers, and mixtures thereof.

6. A composition according to claim 5 wherein said thickening agent is selected from the group consisting of crosslinked polyacrylate polymers, polyacrylamide polymers, and mixtures thereof.

7. A composition according to claim 6 wherein said crosslinked cationic polymer corresponds to the formula $(A)_l(B)_m(C)_n$ wherein (A) is a dialkylaminoalkyl acrylate monomer or its quaternary ammonium or acid addition salt, (B) is a dialkylaminoakyl methacrylate monomer or its quaternary ammonium or acid addition salt, (C) is acrylamide, 1 is an integer of 0 or greater, m is an integer of 1 or great, and n is an integer of 0 or greater, wherein said polymer contains a crosslinking agent.

8. A composition according to claim 7 wherein said crosslinking agent is selected from the group consisting of methylene bisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane, diallylether, allyl sucrose, butadiene, isoprene, divinyl benzene, divinyl naphthalene, allyl acrylate, and mixtures thereof.

9. A composition according to claim 8 wherein said crosslinked cationic polymer is selected from the group consisting of polyquaternium 32, polyquaternium 37, and mixtures thereof.

10. A composition according to claim 6 wherein said polyacrylamide polymer has a molecular weight from about 1,000,000 to about 30,000,000.

11. A composition according to claim 6 wherein said sunscreen active is selected from the group consisting of 2-ethylhexyl p-methoxycinnamate, 4,4'-methoxy-t-butyldibenzoylmethane, zinc oxide, and mixtures thereof.

12. A composition according to claim 11 wherein said hydrophobic structuring agent is selected from the group consisting of stearyl alcohol, cetyl alcohol, behenyl alcohol, polyethylene glycol ether of stearyl alcohol having an average of about 2 ethylene oxide units, and mixtures thereof.

13. A composition according to claim 12 wherein said hydrophilic surfactant is a nonionic surfactant.

14. A composition according to claim 13 wherein said nonionic surfactant is selected from the group consisting of steareth-21, ceteareth-20, ceteareth-12, sucrose cocoate, steareth-100, PEG-100 stearate, and mixtures thereof.

15. A composition according to claim 6 wherein said sunscreen active is selected from the group consisting of 2-ethylhexyl p-methoxycinnamate, 4,4'-methoxy-t-butyldibenzoylmethane, zinc oxide, and mixtures thereof.

16. A composition according to claim 15 wherein the hydrophobic structuring agent is selected from the group consisting of stearyl alcohol, cetyl alcohol, behenyl alcohol, polyethylene glycol ether of stearyl alcohol having an average of about 2 ethylene oxide units, and mixtures thereof.

17. A composition according to claim 16 wherein said hydrophilic surfactant is a nonionic surfactant.

18. A composition according to claim 17 wherein said nonionic surfactant is selected from the group consisting of steareth-21, ceteareth-20, ceteareth-12, sucrose cocoate, steareth-100, PEG-100 stearate, and mixtures thereof.

19. A method for protecting human skin from the harmful effects of UV radiation, said method comprising applying a safe and effective amount of the composition of claim 1 to human skin.

20. A method for lightening human skin, said method comprising applying a safe and effective amount of the composition of claim 1 to human skin.

21. A composition according to claim 1, comprising from about 1% to about 20% of the sunscreen active, from about 1% to about 5% of the hydrophobic structuring agent, from about 0.2% to about 3% of the surfactant, from about 0.25% to about 5% of the thickening agent, from about 1% to about 15% of the skin lightening agent, and from about 60% to about 90% water.

* * * * *

UNITED STATES PATENT AND TRADEMARK OFFICE
CERTIFICATE OF CORRECTION

PATENT NO. : 6,024,942
DATED : February 15, 2000
INVENTOR(S) : Paul Robert Tanner et al.

It is certified that error appears in the above-identified patent and that said Letters Patent is hereby corrected as shown below:

Column 4,
Line 56, "direthylaminobenzoic" should read -- dimethylaminobenzoic --.

Column 5,
Line 17, "thereof" should read -- thereof. --.

Column 7,
Line 25, "aklyl" should read -- alkyl --.
Line 57, "Hiflfer" should read -- Hilfer --

Column 8,
Line 40, "stearamaidopropyl" should read -- stearamidopropyl --.
Line 41, "stearmnidopropyl" should read -- stearamidopropyl --.
Line 61, "cetyl dimethyl" should read -- cetyl ditallow dimethyl --.
Line 62, "dimethyl ammonium" should read -- dicetyl ammonium --.
Lines 62-63 "dimethyl ammonium" should read -- dicetyl ammonium --.
Line 65, "dimethyl methyl" should read -- dicetyl methyl --.
Line 66, "dimethyl methyl" should read -- dicetyl methyl --.

Column 9,
Lines 12-13, "include dimethyl" should read -- include ditallow dimethyl --.
Line 13, "chloride, dimethyl" should read -- chloride, ditallow dimethyl --.
Line 16, "acetate, dimethyl" should read -- acetate, ditallow --.
Line 16, "phosphate, dimethyl" should read -- phosphate, ditallow dimethyl --.
Line 18, "di(coconutalayl)dimethyl" should read -- di(coconutalkyl)dimethyl --.
Lines 22-23, "stearmnidopropyl" should read -- stearamidopropyl --.
Line 31, "chloride, dimethyl" should read -- chloride, dimyristyl dimethyl --.
Line 34, "stermnidopropyl" should read -- stearamidopropyl --.
Line 43, "choride, dimethyl" should read -- chloride, dimyristyl dimethyl --.

Column 11,
Line 1, "coamidopropyl" should read -- cocamidopropyl --.
Lines 4-5, "coamidopropyl" should read -- cocamidopropyl --.

Column 18,
Lines 4-5, "n,n-dethylnicotinamide" should read -- n,n-diethylnicotinamide --.

Column 20,
Line 33, "about but" should read -- about, but --.

UNITED STATES PATENT AND TRADEMARK OFFICE
CERTIFICATE OF CORRECTION

PATENT NO. : 6,024,942
DATED : February 15, 2000
INVENTOR(S) : Paul Robert Tanner et al.

It is certified that error appears in the above-identified patent and that said Letters Patent is hereby corrected as shown below:

Column 21,
Line 42, "harmfull" should read -- harmful --.

Column 22,
Line 1, "0.001%" should read -- 1% --.
Line 7, "thereof, kojic" should read -- thereof; kojic --.
Line 21, "butyidibenzoylmethane" should read -- butyldibenzoylmethane --.

Signed and Sealed this

Twenty-ninth Day of January, 2002

*Attest:*

*Attesting Officer*

JAMES E. ROGAN
*Director of the United States Patent and Trademark Office*